(12) United States Patent
Brannan

(10) Patent No.: US 8,376,948 B2
(45) Date of Patent: *Feb. 19, 2013

(54) ENERGY-DELIVERY DEVICE INCLUDING ULTRASOUND TRANSDUCER ARRAY AND PHASED ANTENNA ARRAY

(75) Inventor: Joseph D. Brannan, Erie, CO (US)

(73) Assignee: Vivant Medical, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/029,521

(22) Filed: Feb. 17, 2011

(65) Prior Publication Data

US 2012/0215103 A1    Aug. 23, 2012

(51) Int. Cl.
*A61B 8/00* (2006.01)
(52) U.S. Cl. .................. 600/439; 600/446; 600/430
(58) Field of Classification Search ................. 600/430, 600/437–469, 407–410, 427, 423; 601/1–3, 601/101–105, 115, 116, 138; 606/41–50
See application file for complete search history.

(56) References Cited

U.S. PATENT DOCUMENTS

| | | | |
|---|---|---|---|
| D223,367 S | 4/1972 | Kountz | |
| D263,020 S | 2/1982 | Rau, III | |
| D266,842 S | 11/1982 | Villers et al. | |
| D278,306 S | 4/1985 | McIntosh | |
| 4,700,716 A | 10/1987 | Kasevich et al. | |
| D295,893 S | 5/1988 | Sharkany et al. | |
| D295,894 S | 5/1988 | Sharkany et al. | |
| 4,776,086 A | 10/1988 | Kasevich et al. | |
| D354,218 S | 1/1995 | Van de Peer | |
| 5,843,144 A * | 12/1998 | Rudie et al. | 607/101 |
| D424,693 S | 5/2000 | Pruter | |
| D424,694 S | 5/2000 | Tetzlaff et al. | |
| D425,201 S | 5/2000 | Tetzlaff et al. | |
| 6,097,985 A | 8/2000 | Kasevich et al. | |
| 6,104,959 A | 8/2000 | Spertell | |
| 6,181,970 B1 | 1/2001 | Kasevich | |
| D449,886 S | 10/2001 | Tetzlaff et al. | |
| D457,958 S | 5/2002 | Dycus et al. | |
| D457,959 S | 5/2002 | Tetzlaff et al. | |
| 6,542,767 B1 | 4/2003 | McNichols et al. | |
| 6,546,934 B1 | 4/2003 | Ingle | |
| 6,575,969 B1 | 6/2003 | Rittman, III | |

(Continued)

FOREIGN PATENT DOCUMENTS

| | | |
|---|---|---|
| CN | 1103807 | 6/1995 |
| DE | 390937 | 3/1924 |

(Continued)

OTHER PUBLICATIONS

U.S. Appl. No. 08/136,098, filed Oct. 14, 1993, Roger A. Stern.

(Continued)

*Primary Examiner* — Sanjay Cattungal
*Assistant Examiner* — Lawrence Laryea

(57) ABSTRACT

A medical device suitable for delivery of energy to tissue includes a housing, a phased antenna array disposed within the housing, and a user-interface coupled to the housing. The user-interface is adapted to enable a user to selectively adjust the radiation pattern of electromagnetic energy delivered into a tissue region by the phased antenna array. The medical device also includes an ultrasound transducer array disposed within the housing. The ultrasound transducer array is configured to acquire data representative of the tissue region during energy delivery into the tissue region by the phased antenna array.

19 Claims, 4 Drawing Sheets

U.S. PATENT DOCUMENTS

| | | | |
|---|---|---|---|
| D487,039 S | 2/2004 | Webster et al. | |
| D496,997 S | 10/2004 | Dycus et al. | |
| D499,181 S | 11/2004 | Dycus et al. | |
| 6,944,504 B1 | 9/2005 | Arndt et al. | |
| 6,957,108 B2 | 10/2005 | Turner et al. | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al | |
| 7,226,446 B1 | 6/2007 | Mody et al. | |
| D564,662 S | 3/2008 | Moses et al. | |
| D576,932 S | 9/2008 | Strehler | |
| 7,439,736 B2 | 10/2008 | Meaney et al. | |
| D594,736 S | 6/2009 | Esjunin | |
| D594,737 S | 6/2009 | Kelly et al. | |
| D606,203 S | 12/2009 | Husheer et al. | |
| D613,412 S | 4/2010 | DeCarlo | |
| D634,010 S | 3/2011 | DeCarlo | |
| 2002/0087151 A1 | 7/2002 | Mody et al. | |
| 2002/0165529 A1 | 11/2002 | Danek | |
| 2003/0109868 A1 | 6/2003 | Chin et al. | |
| 2006/0089624 A1* | 4/2006 | Voegele et al. | 606/1 |
| 2006/0265034 A1 | 11/2006 | Aknine | |
| 2007/0016032 A1* | 1/2007 | Aknine | 600/437 |
| 2007/0276240 A1* | 11/2007 | Rosner et al. | 600/437 |
| 2008/0125772 A1 | 5/2008 | Stone | |
| 2009/0221999 A1 | 9/2009 | Shahidi | |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| EP | 179 607 | 11/1906 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| EP | 1 186 274 | 3/2002 |
| EP | 0 648 515 | 4/2003 |
| FR | 1 275 415 | 10/1961 |
| FR | 1 347 865 | 11/1963 |
| FR | 2 235 669 | 1/1975 |
| FR | 2 276 027 | 1/1976 |
| FR | 2 313 708 | 12/1976 |
| FR | 2 502 935 | 10/1982 |
| FR | 2 517 953 | 6/1983 |
| FR | 2 573 301 | 5/1986 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| JP | 2001231870 | 8/2001 |
| JP | 2008142467 | 6/2008 |
| SU | 166452 | 11/1964 |
| SU | 401367 | 11/1974 |
| SU | 727201 | 4/1980 |
| WO | WO00/28913 | 5/2000 |
| WO | WO00/47283 | 8/2000 |
| WO | WO2007/112081 | 10/2007 |
| WO | WO 2007134256 | 11/2007 |
| WO | WO2010/035831 | 4/2010 |

OTHER PUBLICATIONS

U.S. Appl. No. 08/483,742, filed Jun. 7, 1995, Roger A. Stern.
U.S. Appl. No. 12/619,323, filed Nov. 16, 2009, Arnold V. DeCarlo.
U.S. Appl. No. 12/619,462, filed Nov. 16, 2009, Casey M. Ladtkow.
U.S. Appl. No. 12/620,289, filed Nov. 17, 2009, Joseph D. Brannan.
U.S. Appl. No. 12/642,623, filed Dec. 18, 2009, Prakash Manley.
U.S. Appl. No. 12/686,726, filed Jan. 13, 2010, Joseph D. Brannan.
U.S. Appl. No. 12/692,856, filed Jan. 25, 2010, Joseph D. Brannan.
U.S. Appl. No. 12/696,671, filed Jan. 29, 2010, Steven Kim.
U.S. Appl. No. 12/696,966, filed Jab. 29, 2010, Steven Kim.
U.S. Appl. No. 12/701,030, filed Feb. 5, 2010, Francesca Rossetto.
U.S. Appl. No. 12/708,974, filed Feb. 19, 2010, Joseph D. Brannan.
U.S. Appl. No. 12/709,014, filed Feb. 19, 2010, Joseph D. Brannan.
U.S. Appl. No. 12/712,864, filed Feb. 25, 2010, Joseph D. Brannan.
U.S. Appl. No. 12/713,429, filed Feb. 26, 2010, Anthony C. Lee.
U.S. Appl. No. 12/713,515, filed Feb. 26, 2010, Anthony C. Lee.
U.S. Appl. No. 12/713,641, filed Feb. 26, 2010, Anthony C. Lee.
U.S. Appl. No. 12/719,657, filed Mar. 8, 2010, Mani N. Prakash.
U.S. Appl. No. 12/722,034, filed Mar. 11, 2010, Casey M. Ladtkow.
U.S. Appl. No. 12/731,367, filed Mar. 25, 2010, Joseph D. Brannan.
U.S. Appl. No. 12/732,508, filed Mar. 26, 2010, Steven Kim.
U.S. Appl. No. 12/732,521, filed Mar. 26, 2010, Steven Kim.
U.S. Appl. No. 12/772,675, filed May 3, 2010, Brian Shiu.
U.S. Appl. No. 12/777,984, filed May 11, 2010, Joseph D. Brannan.
U.S. Appl. No. 12/786,671, filed May 25, 2010, Richard A. Willyard.
U.S. Appl. No. 12/787,639, filed May 26, 2010, Mani N. Prakash.
U.S. Appl. No. 12/792,904, filed Jun. 3, 2010, Ronald J. Podhajsky.
U.S. Appl. No. 12/792,932, filed Jun. 3, 2010, Ronald J. Podhajsky.
U.S. Appl. No. 12/792,947, filed Jun. 3, 2010, Ronald J. Podhajsky.
U.S. Appl. No. 12/792,970, filed Jun. 3, 2010, Ronald J. Podhajsky.
U.S. Appl. No. 12/793,037, filed Jun. 3, 2010, Ronald J. Podhajsky.
U.S. Appl. No. 12/823,211, filed Jun. 25, 2010, Mani N. Prakash.
U.S. Appl. No. 12/826,897, filed Jun. 30, 2010, Brian Shiu.
U.S. Appl. No. 12/826,902, filed Jun. 30, 2010, Brian Shiu.
U.S. Appl. No. 12/837,820, filed Jul. 16, 2010, Joseph D. Brannan.

U.S. Appl. No. 12/839,023, filed Jul. 19, 2010, Ronald J. Podhajsky.
U.S. Appl. No. 12/861,333, filed Aug. 23, 2010, Joseph D. Brannan.
U.S. Appl. No. 12/944,951, filed Nov. 12, 2010, Joseph D. Brannan.
U.S. Appl. No. 12/977,390, filed Dec. 23, 2010, Joseph D. Brannan.
U.S. Appl. No. 12/977,415, filed Dec. 23, 2010, Joseph D. Brannan.
U.S. Appl. No. 12/985,124, filed Jan. 5, 2011, Joseph D. Brannan.
U.S. Appl. No. 12/985,136, filed Jan. 5, 2011, Joseph D. Brannan.
U.S. Appl. No. 12/985,155, filed Jan. 5, 2011, Joseph D. Brannan.
U.S. Appl. No. 12/985,179, filed Jan. 5, 2011, Joseph D. Brannan.
U.S. Appl. No. 13/020,562, filed Feb. 3, 2011, Joseph D. Brannan.
U.S. Appl. No. 13/020,664, filed Feb. 3, 2011, Kenlyn S. Bonn.
U.S. Appl. No. 13/024,041, filed Feb. 9, 2011, Joseph D. Brannan.
U.S. Appl. No. 13/029,521, filed Feb. 17, 2011, Joseph D. Brannan.
U.S. Appl. No. 13/029,594, filed Feb. 17, 2011, Joseph D. Brannan.
U.S. Appl. No. 13/043,665, filed Mar. 9, 2011, Richard A. Willyard.
U.S. Appl. No. 13/043,694, filed Mar. 9, 2011, Richard A. Willyard.
U.S. Appl. No. 13/050,729, filed Mar. 17, 2011, Casey M. Ladtkow.
U.S. Appl. No. 13/083,185, filed Apr. 8, 2011, Arnold V. DeCarlo.
U.S. Appl. No. 13/083,256, filed Apr. 8, 2011, Joseph D. Brannan.
U.S. Appl. No. 13/098,199, filed Apr. 29, 2011, Roop L. Mahajan.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Cams et al., "Initial Experience With the LigaSure™ Vessel Sealing System in Abdominal Surgery" Innovations That Work, Jun. 2002.

Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 In Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw•Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., Theoretical Aspects of "Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite•Element Codes to Model Electrical Heating and Nonlinear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure™ Vessel Sealing System in Bloodless Hemorrhoidectomy" Innovations That Work, Mar. 2000.

Joseph G. Andriole M.D. et al., "Biopsy Needle Characteristics Assessed in the Laboratory", Radiology 148: 659-662, Sep. 1983.

Joseph Ortenberg, "LigaSure™ System Used in Laparoscopic 1st and 2nd Stage Orchiopexy" Innovations That Work, Nov. 2002.

K. Ogata, Modern Control Engineering, Prentice-Hall, Englewood Cliffs, N. J., 1970.

Kennedy et al., "High-burst-strength, feedback-controlled bipolar vessel sealing" Surgical Endoscopy (1998) 12: 876-878.

Kopans, D.B. et al., (Nov. 1985) "Spring Hookwire Breast Lesion Localizer: Use with Rigid-Compression. Mammographic Systems," Radiology 157(2):537-538.

Koyle et al., "Laparoscopic Palomo Varicocele Ligation in Children and Adolescents" Pediatric Endosurgery & Innovative Techniques, vol. 6, No. 1, 2002.

LigaSure™ Vessel Sealing System, the Seal of Confidence in General, Gynecologic, Urologic, and Laparaoscopic Surgery, Sales/Product Literature, Jan. 2004.

Livraghi et al., (1995) "Saline-enhanced RF Tissue Ablation in the Treatment of Liver Metastases", Radiology, p. 140 (Abstr).

Lyndon B. Johnson Space Center, Houston, Texas, "Compact Directional Microwave Antenna for Localized Heating," NASA Tech Briefs, Mar. 2008.

M. A. Astrahan, "A Localized Current Field Hyperthermia System for Use with 192-Iridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.

McGahan et al., (1995) "Percutaneous Ultrasound-guided Radiofrequency Electrocautery Ablation of Prostate Tissue in Dogs", Acad Radiol, vol. 2, No. 1: pp. 61-65.

McLellan et al., "Vessel Sealing for Hemostasis During Pelvic Surgery" Int'l Federation of Gynecology and Obstetrics FIGO World Congress 2000, Washington, DC.

MDTECH product literature (Dec. 1999) "FlexStrand": product description, 1 page.

MDTECH product literature (Mar. 2000) I'D Wire: product description, 1 page.

Medtrex Brochure "The O.R. Pro 300" 1 page, Sep. 1998.

Michael Choti, "Abdominoperineal Resection with the LigaSure™ Vessel Sealing System and LigaSure™ Atlas 20 cm Open Instrument" Innovations That Work, Jun. 2003.

Muller et al., "Extended Left Hemicolectomy Using the LigaSure™ Vessel Sealing System" Innovations That Work. LJ, Sep. 1999.

Murakami, R. et al., (1995). "Treatment of Hepatocellular Carcinoma: Value of Percutaneous Microwave Coagulation," American Journal of Radiology (AJR) 164:1159-1164.

Ni Wei et al., "A Signal Processing Method for the Coriolis Mass Flowmeter Based on a Normalized . . . " Journal of Applied Sciences Yingyong Kexue Xuebao, Shangha CN, vol. 23, No. 2:(Mar. 2005); pp. 160-184.

Ogden, "Goertzel Alternative to the Fourier Transform" Jun. 1993 pp. 485-487 Electronics World; Reed Business Publishing, Sutton, Surrey, BG, vol. 99, No. 9, 1687.

Olsson M.D. et al., "Radical Cystectomy in Females" Current Surgical Techniques in Urology, vol. 14, Issue 3, 2001.

Organ, L W., "Electrophysiologic Principles of Radiofrequency Lesion Making" Appl. Neurophysiol, vol. 39: pp. 69-76 (1976/77).

P.R. Stauffer et al., "Interstitial Heating Technologies", Thermoradiotheray and Thermochemotherapy (1995) vol. I, Biology, Physiology, Physics, pp. 279-320.

Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.

Paul G. Horgan, "A Novel Technique for Parenchymal Division During Hepatectomy" The American Journal of Surgery, vol. 181, No. 3, Apr. 2001, pp. 236-237.

Peterson et al., "Comparison of Healing Process Following Ligation with Sutures and Bipolar Vessel Sealing" Surgical Technology International (2001).

R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.

Valleylab Brochure, "Reducing Needlestick Injuries in the Operating Room" 1 page, Mar. 2001.

Reidenbach, (1995) "First Experimental Results with Special Applicators for High-Frequency Interstitial Thermotherapy", Society Minimally Invasive Therapy, 4(Suppl 1):40 (Abstr).

Richard Wolf Medical Instruments Corp. Brochure, "Kleppinger Bipolar Forceps & Bipolar Generator" 3 pages, Jan. 1989.

Rothenberg et al., "Use of the LigaSure™ Vessel Sealing System in Minimally Invasive Surgery in Children" Int'l Pediatric Endosurgery Group (I PEG) 2000.

Sayfan et al., "Sutureless Closed Hemorrhoidectomy: A New Technique" Annals of Surgery, vol. 234, No. 1, Jul. 2001, pp. 21-24.

Sengupta et al., "Use of a Computer-Controlled Bipolar Diathermy System in Radical Prostatectomies and Other Open Urological Surgery" ANZ Journal of Surgery (2001) 71.9 pp. 538-540.

Sigel et al., "The Mechanism of Blood Vessel Closure by High Frequency Electrocoagulation" Surgery Gynecology & Obstetrics, Oct. 1965 pp. 823-831.

Solbiati et al., (2001) "Percutaneous Radio-frequency Ablation of Hepatic Metastases from Colorectal Cancer: Long-term Results in 117 Patients", Radiology, vol. 221, pp. 159-166.

Solbiati et al. (1995) "Percutaneous US-guided RF Tissue Ablation of Liver Metastases: Long-term Follow-up", Radiology, pp. 195-203.

Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.

Stuart W. Young, Nuclear Magnetic Resonance Imaging--Basic Principles, Raven Press, New York, 1984.

Sugita et al., "Bipolar Coagulator with Automatic Thermocontrol" J. Neurosurg., vol. 41, Dec. 1944, pp. 777-779.

Sylvain Labonte et al., "Monopole Antennas for Microwave Catheter Ablation", IEEE Trans. on Microwave Theory and Techniques, vol. 44, No, 10, pp. 1832-1840, Oct. 1995.

T. Matsukawa et al., "Percutaneous Microwave Coagulation Therapy in Liver Tumors", Acta Radiologica, vol. 38, pp. 410-415, 1997.

T. Seki et al., (1994) "Ultrasonically Guided Percutaneous Microwave Coagulation Therapy for Small Hepatocellular Carcinoma," Cancer 74(3):817-825.

Urologix, Inc.-Medical Professionals: Targis™ Technology (Date Unknown). "Overcoming the Challenge" located at: <http://www.urologix.com!medicaUtechnology.html > last visited on Apr. 27, 2001, 3 pages.

Urrutia et al., (1988). "Retractable-Barb Needle for Breast Lesion Localization: Use in 60 Cases," Radiology 169(3):845-847.

Valleylab Brochure, "Valleylab Electroshield Monitoring System" 2 pages, Nov. 1995.

ValleyLab Brochure, "Electosurgery: A Historical Overview", Innovations in Electrosurgery, 1999.

Vallfors et al., "Automatically Controlled Bipolar Electrocoagulation-'COA-COMP'" Neurosurgical Review 7:2-3 (1984) pp. 187-190.

W. Scott Helton, "LigaSure™ Vessel Sealing System: Revolutionary Hemostasis Product for General Surgery" Sales/Product Literature 1999.

Wald et al., "Accidental Burns", JAMA, Aug. 16, 1971, vol. 217, No. 7, pp. 916-921.

Walt Boyles, "Instrumentation Reference Book", 2002, Butterworth-Heinemann, pp. 262-264.

Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.

European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.

European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004974.5 dated Apr. 6, 2011.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09012389.4 dated Jul. 6, 2010.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.
European Search Report EP 10005533.4 extended dated Sep. 24, 2010.
European Search Report EP 10005534.2 extended dated Sep. 17, 2010.
European Search Report EP 10006373.4 extended dated Nov. 11, 2010.
European Search Report EP 10008139.7 extended dated Nov. 30, 2010.
European Search Report EP 10008140.5 extended dated Dec. 28, 2010.
European Search Report EP 10008850.9 extended dated Nov. 30, 2010.
European Search Report EP 10009731.0 extended dated Jan. 28, 2011.
European Search Report EP 10009732.8 extended dated Jan. 26, 2011.
European Search Report EP 10010943.8 extended dated Feb. 1, 2011.

European Search Report EP 10011750.6 extended dated Feb. 1, 2011.
European Search Report EP 10014042.5 extended dated Feb. 18, 2011.
European Search Report EP 10158944.8 extended dated Jun. 21, 2010.
European Search Report EP 10161722.3 extended dated Jun. 16, 2010.
European Search Report EP 10163235.4 dated Aug. 10, 2010.
European Search Report EP 10185413.1 dated Dec. 7, 2010.
European Search Report EP 10185413.1 dated Mar. 14, 2011.
European Search Report EP 10191321.8 dated Apr. 7, 2011.
International Search Report PCT/US97/05066 dated Jun. 24, 1997.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.
European Search Report for European Application No. 12000984.0 dated Jun. 25, 2012.
European Search Report for European Application No. 12000985.7 dated May 8, 2012.

* cited by examiner

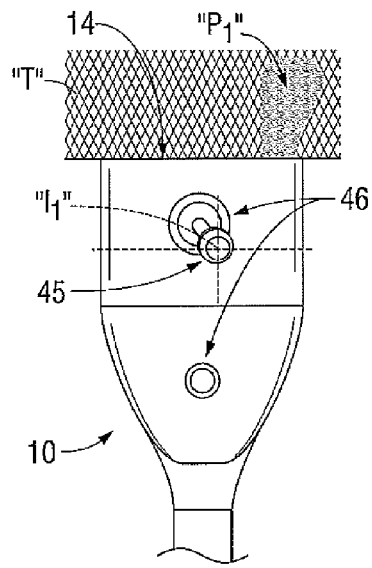
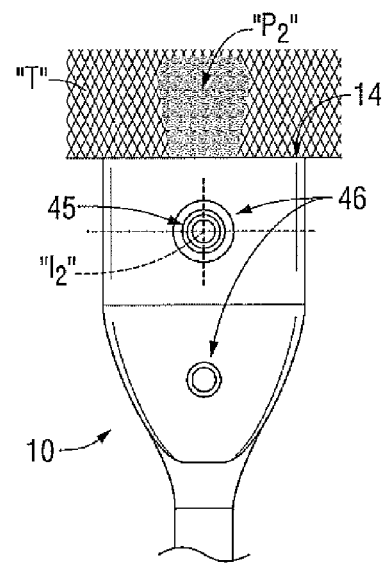
FIG. 4　　　　　　　　　FIG. 5
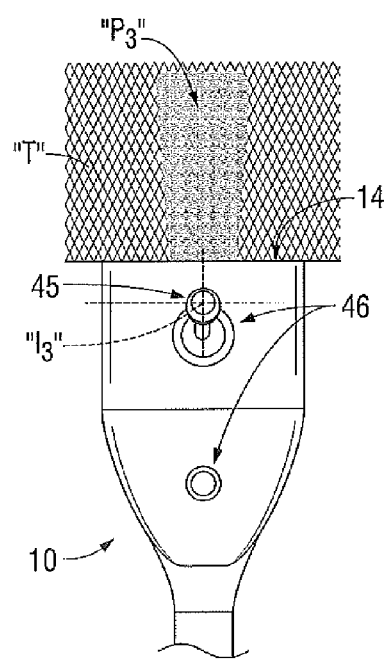
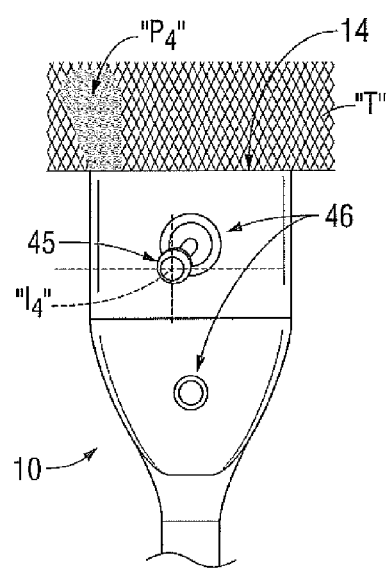
FIG. 6　　　　　　　　　FIG. 7

ENERGY-DELIVERY DEVICE INCLUDING ULTRASOUND TRANSDUCER ARRAY AND PHASED ANTENNA ARRAY

BACKGROUND

1. Technical Field

The present disclosure relates to electrosurgical devices suitable for tissue ablation applications and, more particularly, to an energy-delivery device including an ultrasound transducer array and a phased antenna array and systems including the same.

2. Discussion of Related Art

Treatment of certain diseases requires the destruction of malignant tissue growths, e.g., tumors. Electromagnetic radiation can be used to heat and destroy tumor cells. Treatment may involve inserting ablation probes into tissues where cancerous tumors have been identified. Once the probes are positioned, electromagnetic energy is passed through the probes into surrounding tissue.

In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperatures above 41° C. while maintaining adjacent healthy cells below the temperature at which irreversible cell destruction occurs. These methods involve applying electromagnetic radiation to heat, ablate and/or coagulate tissue. Microwave energy is sometimes utilized to perform these methods. Other procedures utilizing electromagnetic radiation to heat tissue also include coagulation, cutting and/or ablation of tissue.

Electrosurgical devices utilizing electromagnetic radiation have been developed for a variety of uses and applications. A number of devices are available that can be used to provide high bursts of energy for short periods of time to achieve cutting and coagulative effects on various tissues. There are a number of different types of apparatus that can be used to perform ablation procedures. Typically, microwave apparatus for use in ablation procedures include a microwave generator that functions as an energy source, and a microwave surgical instrument (e.g., microwave ablation probe) having an antenna assembly for directing energy to the target tissue. The microwave generator and surgical instrument are typically operatively coupled by a cable assembly having a plurality of conductors for transmitting microwave energy from the generator to the instrument, and for communicating control, feedback and identification signals between the instrument and the generator.

There are several types of microwave probes in use, e.g., monopole, dipole and helical, which may be used in tissue ablation applications. In monopole and dipole antenna assemblies, microwave energy generally radiates perpendicularly away from the axis of the conductor. Monopole antenna assemblies typically include a single, elongated conductor. A typical dipole antenna assembly includes two elongated conductors that are linearly-aligned and positioned end-to-end relative to one another with an electrical insulator placed therebetween. Helical antenna assemblies include helically-shaped conductor configurations of various dimensions, e.g., diameter and length. The main modes of operation of a helical antenna assembly are normal mode (broadside), in which the field radiated by the helix is maximum in a perpendicular plane to the helix axis, and axial mode (end fire), in which maximum radiation is along the helix axis.

During certain procedures, a probe may be inserted directly into tissue, inserted through a lumen, e.g., a vein, needle or catheter, or placed into the body using surgical techniques. Ultrasound or computed tomography (CT) guidance may used prior to ablation treatments for aiding probe placement. Multiple probes may be used to synergistically create a large ablation or to ablate separate sites simultaneously.

The particular type of tissue ablation procedure may dictate a particular ablation volume in order to achieve a desired surgical outcome. Ablation volume is correlated with antenna design, antenna performance, antenna impedance, number of energy applicators used simultaneously, ablation time and wattage, and tissue characteristics, e.g., tissue impedance. During certain procedures, it can be difficult to assess the extent to which the microwave energy will radiate into the surrounding tissue, making it difficult to determine the area or volume of surrounding tissue that will be ablated.

Because of the small temperature difference between the temperature required for denaturing malignant cells and the temperature normally injurious to healthy cells, a known heating pattern and precise temperature control is needed to lead to more predictable temperature distribution to eradicate abnormal tissue structures, such as tumors, while minimizing the damage to surrounding normal tissue.

SUMMARY

The present disclosure relates to a medical device suitable for delivery of energy to tissue including a housing, a phased antenna array disposed within the housing, and a user-interface coupled to the housing. The user-interface is adapted to enable a user to selectively adjust the radiation pattern of electromagnetic energy delivered into a tissue region by the phased antenna array. The medical device also includes an ultrasound transducer array disposed within the housing. The ultrasound transducer array is configured to acquire data representative of the tissue region during energy delivery into the tissue region by the phased antenna array.

The present disclosure also relates to a system including a electrosurgical power generating source and a hand-holdable device operably associated with the electrosurgical power generating source. The hand-holdable device includes a phased antenna array, a user-interface coupled adapted to enable a user to selectively adjust the radiation pattern of electromagnetic energy delivered into a tissue region by the phased antenna array, and an ultrasound transducer array configured to acquire data representative of the tissue region during energy delivery into the tissue region by the phased antenna array.

BRIEF DESCRIPTION OF THE DRAWINGS

Objects and features of the presently-disclosed energy-delivery device including a ultrasound transducer array and a phased antenna array and systems including the same will become apparent to those of ordinary skill in the art when descriptions of various embodiments thereof are read with reference to the accompanying drawings, of which:

FIG. 4 is a top, perspective view of the medical device of FIG. 1 showing the pointing device of FIG. 2 positioned in a first indicative orientation and showing a diagrammatic representation of a radiation pattern of electromagnetic energy delivered into tissue by the medical device responsive to the first indicative orientation of the pointing device in accordance with an embodiment of the present disclosure;

FIG. 5 is a top, perspective view of the medical device of FIG. 1 showing the pointing device of FIG. 2 positioned in a second indicative orientation and showing a diagrammatic representation of a radiation pattern of electromagnetic energy delivered into tissue by the medical device responsive to the second indicative orientation of the pointing device in accordance with an embodiment of the present disclosure;

FIG. 6 is a top, perspective view of the medical device of FIG. 1 showing the pointing device of FIG. 2 positioned in a third indicative orientation and showing a diagrammatic representation of a radiation pattern of electromagnetic energy delivered into tissue by the medical device responsive to the third indicative orientation of the pointing device in accordance with an embodiment of the present disclosure;

FIG. 7 is a top, perspective view of the medical device of FIG. 1 showing the pointing device of FIG. 2 positioned in a fourth indicative orientation and showing a diagrammatic representation of a radiation pattern of electromagnetic energy delivered into tissue by the medical device responsive to the fourth indicative orientation of the pointing device in accordance with an embodiment of the present disclosure.

DETAILED DESCRIPTION

Figure 1:
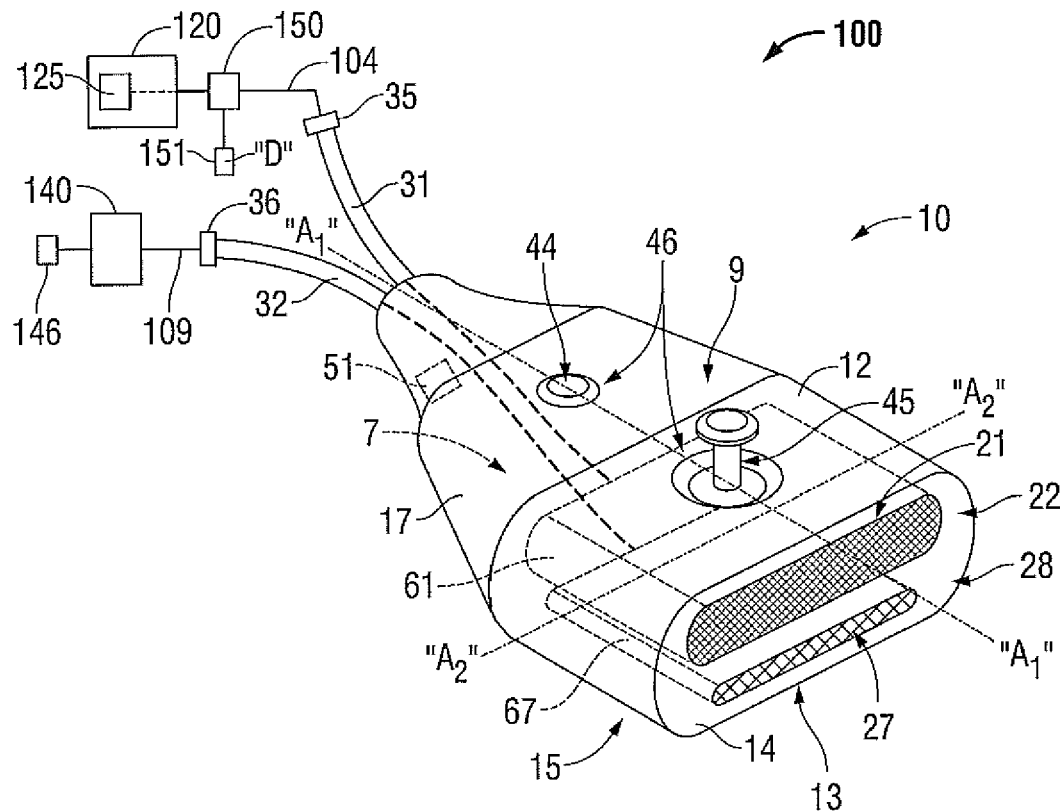
FIG. 1 is a perspective and schematic view of a system including an energy-delivery (medical) device including an ultrasound transducer array and a phased antenna array in accordance with an embodiment of the present disclosure.

Hereinafter, embodiments of an energy-delivery device (also referred to herein as a "medical device" or a "handheld device") including an ultrasound transducer array and a phased antenna array and systems including the same of the present disclosure are described with reference to the accompanying drawings. Like reference numerals may refer to similar or identical elements throughout the different views of the figures. As shown in the drawings and as used in this description, and as is traditional when referring to relative positioning on an object, the term "proximal" refers to that portion of the apparatus, or component thereof, closer to the user and the term "distal" refers to that portion of the apparatus, or component thereof, farther from the user.

This description may use the phrases "in an embodiment," "in embodiments," "in some embodiments," or "in other embodiments," which may each refer to one or more of the same or different embodiments in accordance with the present disclosure. For the purposes of this description, a phrase in the form "A/B" means A or B. For the purposes of the description, a phrase in the form "A and/or B" means "(A), (B), or (A and B)". For the purposes of this description, a phrase in the form "at least one of A, B, or C" means "(A), (B), (C), (A and B), (A and C), (B and C), or (A, B and C)".

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3\times10^8$ cycles/second) to 300 gigahertz (GHz) ($3\times10^{11}$ cycles/second).

As it is used in this description, "ablation procedure" generally refers to any ablation procedure, such as, for example, microwave ablation, radiofrequency (RF) ablation, or microwave or RF ablation-assisted resection. As it is used in this description, "energy applicator" generally refers to any device that can be used to transfer energy from a power generating source, such as a microwave or RF electrosurgical generator, to tissue. For the purposes herein, the term "energy applicator" is interchangeable with the term "energy-delivery device". As it is used in this description, "transmission line" generally refers to any transmission medium that can be used for the propagation of signals from one point to another.

As it is used in this description, "phased antenna array" generally refers to any multi-element antenna array capable of shifting the phase of the signal emitted from each radiating element, to provide constructive/destructive interference so as to steer the antenna beam in the desired direction. For the purposes herein, the term "radiating element" is interchangeable with the term "antenna element". As it is used in this description, "electromagnetic window" generally refers to any and all types of radomes and windows through which electromagnetic signals are passed in use.

As it is used in this description, "length" may refer to electrical length or physical length. In general, electrical length is an expression of the length of a transmission medium in terms of the wavelength of a signal propagating within the medium. Electrical length is normally expressed in terms of wavelength, radians or degrees. For example, electrical length may be expressed as a multiple or sub-multiple of the wavelength of an electromagnetic wave or electrical signal propagating within a transmission medium. The wavelength may be expressed in radians or in artificial units of angular measure, such as degrees. The electric length of a transmission medium may be expressed as its physical length multiplied by the ratio of (a) the propagation time of an electrical or electromagnetic signal through the medium to (b) the propagation time of an electromagnetic wave in free space over a distance equal to the physical length of the medium. The electrical length is in general different from the physical length. By the addition of an appropriate reactive element (capacitive or inductive), the electrical length may be made significantly shorter or longer than the physical length.

As used in this description, the term "real-time" means generally with no observable latency between data processing and display. As used in this description, "near real-time" generally refers to a relatively short time span between the time of data acquisition and display.

Various embodiments of the present disclosure provide an ultrasound transducer array and a phased antenna array incorporated into one, direct-to-patient contact device capable of directing electromagnetic energy into tissue. The presently-disclosed energy-delivery devices including an ultrasound transducer array and a phased antenna array are adapted to enable user control of the radiation pattern of electromagnetic energy delivered into tissue, and may be suitable for use in a variety of procedures and operations. Various embodiments of the presently-disclosed energy-delivery device including an ultrasound transducer array and a phased antenna array are adapted to be hand-holdable and include an ergonomically located user-interface.

Various embodiments of the presently-disclosed energy-delivery device including an ultrasound transducer array and a phased antenna array are adapted to enable user-controllable focal location of electromagnetic energy delivery into tissue to depths ranging from about one centimeter (cm) to about three centimeters, e.g., in relation to a tissue surface, at an operational frequency between about 1 GHz and about 5

GHz. Embodiments may enable user-controllable focal location of electromagnetic energy delivery into tissue to a variable predetermined depth or range of depths. In the case of a 3 cm ablation that is focally located 3 cm deep, for example, tissue 4.5 cm deep can be treated. By enlarging the device, decreasing operational frequency and/or increasing the number of array elements, deeper tissue may be treatable. In some embodiments, data acquired by the ultrasound transducer array may be outputted from the energy-delivery device to an ultrasound imaging system, and may be outputted from the imaging system to one or more display devices, which may be used by the clinician to visualize the targeted region in real-time and/or near real-time.

The presently-disclosed energy-delivery device including an ultrasound transducer array and a phased antenna array according to various embodiments is designed and configured to operate between about 300 MHz and about 10 GHz. Embodiments may be implemented using electromagnetic radiation at microwave frequencies, RF frequencies or at other frequencies.

Various embodiments of the presently-disclosed energy-delivery device including an ultrasound transducer array and a phased antenna array are suitable for microwave or RF ablation and for use to pre-coagulate tissue for microwave or RF ablation-assisted surgical resection. Although various methods described hereinbelow are targeted toward microwave ablation and the complete destruction of target tissue, it is to be understood that methods for directing electromagnetic radiation may be used with other therapies in which the target tissue is partially destroyed or damaged. In addition, although the following description describes the use of a microwave phased antenna array, the teachings of the present disclosure may also apply to other type of user-controllable phased antenna array.

An electrosurgical system including an energy-delivery device including an ultrasound transducer array and a phased antenna array according to various embodiments is capable of providing real-time and/or near real-time image feedback during electromagnetic energy-induced thermal therapy, e.g., to allow the clinician to better visualize and understand how to achieve more optimized results during thermal treatment of tissue.

FIG. 1 shows an electrosurgical system (shown generally as 100) according to an embodiment of the present disclosure that includes an energy-delivery device 10 including an ultrasound transducer array 67 and a microwave phased antenna array 61. Microwave phased antenna array 61 generally includes a plurality of radiating elements (e.g., "$A_1$", "$A_2$", "$A_3$", "$A_4$" through "$A_N$" shown in FIG. 3) positioned to form a desired number of rows and columns. In some embodiments, the radiating elements may be aperture (waveguide) or linear (dipole) antennas operating at S, L, or C band frequencies. In some embodiments, the radiating elements may be spiral, dipole, slot, or any type of microstrip antenna, e.g., a patch antenna (also known as a rectangular microstrip antenna), and may be formed on a substrate, such as a dielectric sheet material, e.g., using conventional printed circuit board (PCB) fabrication techniques.

Ultrasound transducer device 67 (also referred to herein as an "ultrasound transducer array") may be any suitable device capable of generating, transmitting and receiving ultrasound waves. Ultrasound transducer device 67 may include a one-dimensional or multi-dimensional array of transducer elements (not shown). Ultrasound transducer device 67 may be adapted for amplifying the reflected ultrasound signal received by the ultrasound transducer device 67. In some embodiments, ultrasound transducer array 67 includes a plurality of transducer elements that are individually controllable and operable to form a two-dimensional array, e.g., suitable for scanning a volumetric region in three dimensions. Individual transducer elements may be individually selectable and operable together to form a one-dimensional array, e.g., suitable for scanning a planar region in two dimensions. Ultrasound transducer array 67 may be adapted to produce an image over a wide field of view, such as a sector scan image produced by repeatedly transmitting and receiving ultrasound energy in radial directions from the medical device 10. Ultrasound imaging may allow the clinician to observe the relationship between abnormal tissue structures, such as tumors, and normal tissue structures, such as vessels and tissue boundaries, during treatments.

Energy-delivery device 10 includes a housing 15 generally defining a first axis "$A_1$"-"$A_1$", e.g., a central longitudinal axis, and a second axis "$A_2$"-"$A_2$" disposed perpendicular to the first axis "$A_1$"-"$A_1$". In some embodiments, the housing 15 is formed from two housing halves (not shown). Each half of the housing 15 may include a series of mechanical interfacing components (not shown) configured to matingly engage with a corresponding series of mechanical interfaces (not shown) to align the two housing halves about the inner components and assemblies of the energy-delivery device 10.

As shown in FIG. 1, the housing 15 includes a body member 17 including a distal end 13. Body member 17 defines a tissue-contact surface 14 at the distal end 13, a top surface 12 including a distal edge coupled to the tissue-contact surface 14, and an internal chamber 7 configured to contain the ultrasound transducer device 67 and the microwave phased antenna array 61 therein. Tissue-contact surface 14 may have any suitable configuration, e.g., a flat, planar or curved configuration, and may be disposed generally perpendicular to the top surface 12.

Tissue-contact surface 14 generally includes one or more regions defining one or more electromagnetic windows through which electromagnetic signals are passed in use. In some embodiments, the tissue-contact surface 14 includes a first region 28 defining an ultrasound transmissive window 27 and a second region 22 defining a microwave transmissive window 21. As shown in FIG. 1, the first region 28 corresponds to a lower portion of the tissue-contact surface 14, and the second region 22 corresponds to an upper portion of the tissue-contact surface 14. Ultrasound transducer device 67 operations may involve directing ultrasound energy through the ultrasound transmissive window 27 and receiving ultrasound energy through the ultrasound transmissive window 27.

Ultrasound transmissive window 27 and the microwave transmissive window 21 may be composed of low-loss dielectric materials. It will be appreciated that the ultrasound transmissive window 27 and the microwave transmissive window 21 may be disposed in any suitable relation to one another, such as one above (or below) the other, and may have any suitable shape, e.g., depending on the particular configuration of the ultrasound transducer device 67 and/or the microwave phased antenna array 61 housed within the body member 17.

Body member 17, or portion thereof, may be formed from metal, thermoplastic, e.g., polycarbonate, composites, e.g., plastic-metal or ceramic-metal composites, or other materials, and may be configured to be hand-holdable. The design and/or material of the ultrasound transmissive window 27 and the microwave transmissive window 21 may differ compared to one or more structural parts of the tissue-contact surface 14, e.g., to achieve desired electrical performance. The size and shape of the housing 15 may be varied from the configuration depicted in FIG. 1.

As shown in FIG. 1, electrosurgical system 100 generally includes an electrosurgical power generating source 120, e.g., a microwave or RF electrosurgical generator, a user-interface 46 associated with the energy-delivery device 10, and a processor unit 150 communicatively coupled with the phased antenna array 61. User-interface 46 may be communicatively coupled with the processor unit 150 and/or other processor unit (not shown). Electrosurgical system 100 may include an ultrasonic imaging system 140 communicatively coupled with the ultrasound transducer array 67. Ultrasonic imaging system 140 may be connected to one or more display devices and/or screens 146 (e.g., LCD (liquid crystal display), plasma, OLED (organic light emitting diode), holographic, flat, and the like) for displaying output from the ultrasonic imaging system 140, which may allow clinicians to visualize the ablative process in real-time and/or near real-time.

User-interface 46 may be adapted to cooperatively operate with the processor unit 150 and/or other processor (not shown) to enable the user to selectively-control one or more parameters of electromagnetic energy delivery into tissue by the medical device 10. User-interface 46 may be disposed on, or otherwise associated with, the housing 15, e.g., ergonomically located on the top surface 12 of the body member 17. In some embodiments, the user-interface 46 includes a pointing device 45, e.g., a joystick, trackball, or the like, communicatively coupled to the processor unit 150.

In some embodiments, user-effected movement of the pointing device 45 is defined with respect to "X" and "Y" axes (schematically shown by double arrowheaded lines in FIG. 2), representative of indicative orientations of the pointing device 45. The axis "Y" may be oriented in a direction parallel to the first axis "$A_1$"-"$A_1$" of the housing 15, and the axis "X" may be oriented in a direction parallel to the second axis "$A_2$"-"$A_2$" of the housing 15. As described in more detail later in this description, one or more parameters of electromagnetic energy delivery into tissue by the medical device 10 may be correlated to the indicative orientations of the pointing device 45.

Pointing device 45 may be ergonomically located on the top surface 12 of the body member 17 such that the user can control the pointing device 45 easily with thumb, finger, or palm. As an alternative to (or in addition to) the pointing device 45, the user-interface 46 may include voice input technology, including, for example, hardware and/or software incorporated in the processor unit 150, or a separate digital module connected to the processor unit 150. The voice input technology may include voice recognition, voice activation, voice rectification, and/or embedded speech.

User-interface 46 may additionally, or alternatively, include a power on/off switch 44. The power on/off switch 44 may be disposed on, or otherwise associated with, the housing 15, e.g., ergonomically located on the top surface 12, and may have any suitable configuration, e.g., rotatable knobs, depressable buttons, toggle switches, slide switches, voice or sound actuated switches, or any other suitable device capable of turning off power to the medical device 10. The power on/off switch 44 may be implemented as a remotely operable device, such as a footswitch, a handswitch, or an orally-activated switch. User-interface 46 may additionally, or alternatively, include an indicator (not shown), such as an audible and/or visual indicator, e.g., an illuminated indicator (e.g., a single- or variably-colored LED indicator), to alert or signal the user that power is turned on/off.

User-interface 46 may be adapted to cooperatively operate with the processor unit 150 to enable the user to selectively-steer the focal point of energy delivery in tissue to various locations and/or to enable the user to the control the energy deposition pattern, e.g., an ablation field radiating into tissue. One or more electrical signals outputted from the user-interface 46, e.g., responsive to a user-effected movement of the pointing device 45, received by the processor unit 150 may be used to determine and set the phasing of radiating elements of the microwave phased antenna array 61, e.g., to allow the focal point of energy delivery in tissue to be varied in position in real-time and/or near real-time.

Processor unit 150 may include any type of computing device, computational circuit, or any type of processor or processing circuit capable of executing a series of instructions that are stored in a memory, e.g., memory 151, associated with the processor unit 150. Processor unit 150 may be adapted to run an operating system platform and application programs. Although the processor unit 150 is illustrated as a standalone module in FIG. 1, it is to be understood that the processor unit 150 may be integrated fully or partially into the electrosurgical power generating source 120, or other component of the electrosurgical system 100. Medical device 10 may be configured with a memory 51 disposed within the body member 17 and communicatively coupled with the processor unit 150 and/or communicatively coupled with an internal processor (not shown).

Processor unit 150 may receive user inputs from the user-interface 46, such as an electric signal indicative of the position and/or a relative movement of the pointing device 45, e.g., a joystick or trackball, and/or other device communicatively coupled to the processor unit 150. In some embodiments, data "D" (representative of a mapping of the indicative orientations of the pointing device 45 to settings for properly phasing the phased antenna array 61 to achieve desired radiation patterns) is stored in a suitable memory for use by the processor 150, e.g., to enable steering of the beam and/or the focal point of energy delivery in the desired direction and/or to the desired location in tissue. Data "D" may be stored in any suitable data structure, such as a look-up table or other data structure. Data "D" may be stored in a memory 51 (internal to medical device 10) and/or stored in a memory 151 (external to medical device 10). In some embodiments, data "D" may be stored in a library (not shown) communicatively coupled to processor 150. As it is used in this description, "library" generally refers to any repository, databank, database, cache, storage unit and the like.

Electrosurgical power generating source 120 may be any generator suitable for use with electrosurgical devices, and may be configured to provide various frequencies of electromagnetic energy. In some embodiments, the electrosurgical power generating source 120 is configured to provide microwave energy at an operational frequency from about 300 MHz to about 10 GHz. An example of an electrosurgical generator that delivers 915 MHz, which may be suitable for use as a source of electrosurgical energy, is commercially available under the trademark EVIDENT™ Microwave Ablation Generator offered by Covidien.

Electrosurgical power generating source 120 may include a user-interface 125 in operable communication with processor unit 150. Electrosurgical power generating source 120 may include a database configured to store and retrieve energy applicator data, e.g., parameters associated with one or more energy-delivery devices. In use, the clinician may interact with the user-interface 125 to preview operational characteristics of an energy-delivery device, such as, for example, medical device 10. User-interface 125 may include a display device (not shown) adapted to visually display one or more user-interface elements. The display device may include touchscreen capability, e.g., the ability to receive user input through direct physical interaction with the display device, e.g., by contacting the display panel of the display device with a stylus or fingertip.

Microwave phased antenna array 61 may be operably coupled to the processor unit 150 and/or the electrosurgical power generating source 120 by a cable connection or a wireless connection, e.g., a radiofrequency or infrared link. In some embodiments, energy-delivery device 10 includes a first cable assembly 31 operably coupled to a first connector 35, which further operably connects the phased antenna array 61 via a first transmission line 104 to the processor unit 150. First cable assembly 31 may have a proximal end suitable for connection to the electrosurgical energy source 120.

Energy-delivery device 10 may additionally, or alternatively, include a second cable assembly 32 operably coupled to a second connector 36, which further operably connects the ultrasound transducer device 61 via a second transmission line 109 to the ultrasonic imaging system 140. Second cable assembly 32 may have a proximal end suitable for connection to the ultrasonic imaging system 140.

In some embodiments, data acquired from the ultrasound transducer array 61 is outputted from the energy-delivery device 100 to the ultrasound imaging system 140, e.g., for processing to provide an image format suitable for display, and may be outputted from the imaging system 140 to one or more display devices 146, which may be used by the clinician to visualize the targeted region and/or the ablation isotherm volume in real-time or near real-time during a procedure. During activation of the ultrasound transducer array 61, a bubble field or cloud of micro-fine bubbles may be generated in the targeted region, e.g., resulting from thermally-induced mass phase transition (e.g., liquid-gas phase transition), and may be visibly observable within the ultrasound imaging. Observation of the temporal evolution and spatial distribution of the bubble cloud generated in the target region may allow clinicians to better visualize and understand how to achieve more optimized results during thermal treatment of tissue, e.g., to allow clinicians to avoid ablating sensitive structures, such as large vessels, healthy organs or vital membrane barriers.

Electrosurgical system 100 may include a coolant supply system (e.g., 350 shown in FIG. 3) coupled in fluid communication with one or more components of the medical device 10. In some embodiments, the coolant supply system may be adapted to circulate coolant fluid (e.g., "F" shown in FIG. 3) into and out of an electromagnetic window (e.g., 390 shown in FIG. 3) disposed at the distal end 13 of the housing 15.

During microwave ablation, e.g., using the electrosurgical system 100, the medical device 10 is placed adjacent to tissue and microwave energy is supplied thereto. A clinician may pre-determine the length of time that microwave energy is to be applied. Application duration may depend on many factors such as tumor size and location and whether the tumor was a secondary or primary cancer. The duration of microwave energy application using the medical device 10 may depend on the progress of the heat distribution within the tissue area that is to be destroyed and/or the surrounding tissue. Treatment of certain tumors may involve probe repositioning during the ablation procedure, such as where the tumor is larger than the probe or has a shape that does not correspond with available probe geometry or radiation pattern.

Figure 2:
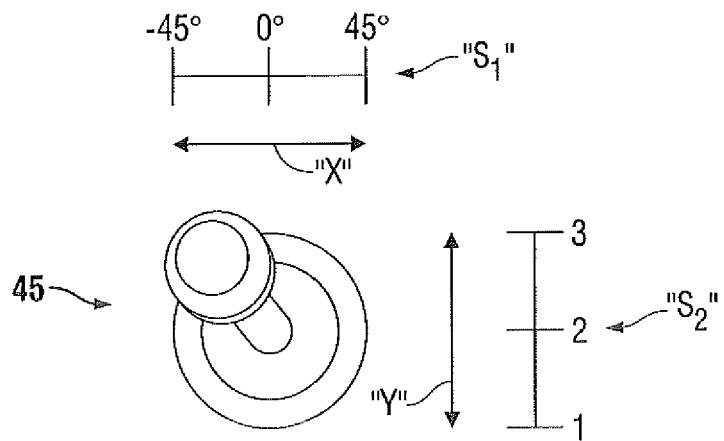
FIG. 2 is an enlarged, perspective view of a pointing device shown with two schematically-illustrated axis (shown by double arrowheaded lines) representative of indicative orientations of the pointing device in accordance with an embodiment of the present disclosure.

User-interface 46 may include indicia thereon representative of one or more user-selectable parameters of electromagnetic energy delivery into tissue by the medical device 10, e.g., a first scale "$S_1$" and a second scale "$S_2$". As shown in FIG. 2, the first scale "$S_1$" includes indicia graduation marks and angle in degrees (e.g., 45°, 0°, 45°), and the second scale "$S_2$" includes indicia graduation marks and a series of consecutive positive integers (e.g., 1, 2, 3) corresponding to increasing levels of energy intensity indicative of energy intensity levels. The indicia may be etched, stamped, formed or the like, e.g., on the upper surface 12 and neighboring the pointing device 45. The design of the indicia may be varied from the configuration depicted in FIG. 2.

One or more parameters of electromagnetic energy delivery into tissue by the medical device 10 may be correlated to indicative orientations of the pointing device 45. User-effected movement of the pointing device 45 may be defined in terms of movement in a first direction (e.g., an X-axis direction) and movement in a second direction (e.g., a Y-axis direction) perpendicular to the first direction. Signals outputted from the pointing device 45 representative of indicative orientations of the pointing device 45 may be correlated to one or more parameters of electromagnetic energy delivery into tissue.

In some embodiments, user-effected movement of the pointing device 45 in a first direction (e.g., an X-axis direction), a second direction (e.g., a Y-axis direction) and/or a third direction (e.g., a Z-axis direction) is correlated to a predetermined phasing of the phased antenna array 61, to enable steering of the beam and/or steering of the focal point of energy delivery by the medical device 10 in the desired direction and/or to the desired location in tissue "T".

In some embodiments, medical device 10 is configured to adjust power parameters (e.g., voltage, power and/or current intensity) and/or the power versus impedance curve shape to affect the perceived output intensity, responsive to user-effected movement of the pointing device 45 in a first direction (e.g., an X-axis direction). For example, the greater the lateral displacement of the pointing device 45 in a distal direction, the greater the level of the power parameters transmitted to the phased antenna array 61. Intensity settings may be preset and selected from a look-up table, e.g., based on a configuration of the radiating elements of the phased antenna array 61, desired surgical effect, surgical specialty and/or surgeon preference. The selection may be made automatically or selected manually by the user. The intensity values may be predetermined or adjusted by the user.

Figure 3:
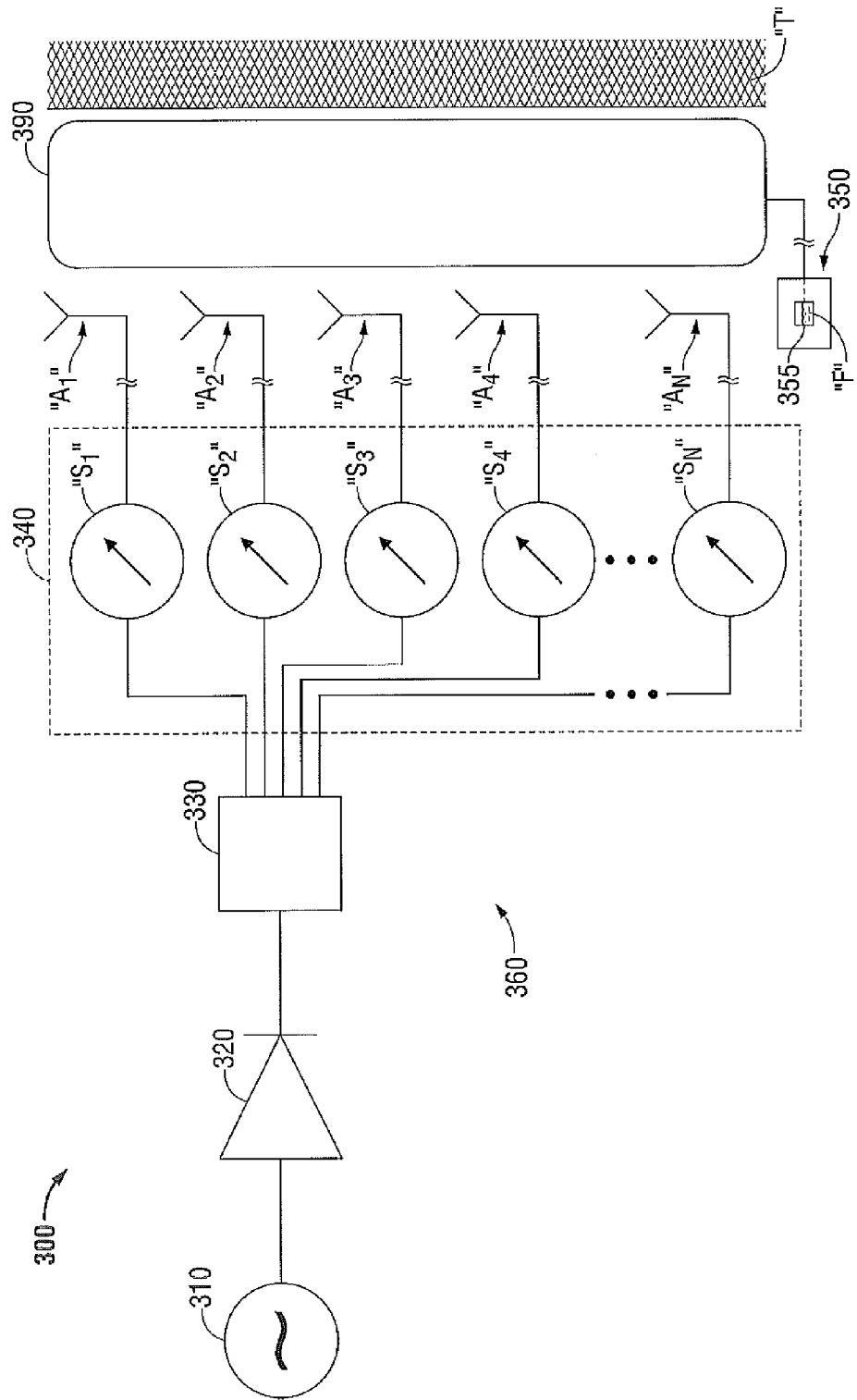
FIG. 3 is a schematic diagram of an energy-delivery system including a radiant electromagnetic energy transmissive structure disposed at the distal end of a phased antenna array in accordance with an embodiment of the present disclosure.

FIG. 3 is schematic diagram of an embodiment of an energy-delivery system (shown generally as 300) that includes a signal source 310, a phased antenna array 360 coupled to the signal source 310, and a radiant electromagnetic energy transmissive structure 390 (also referred to herein as an "electromagnetic window") disposed at the distal end of the phased antenna array 360. Signal source 310 is generally configured to provide microwave frequency output signals.

Phased antenna array 360 includes a microwave amplifier unit 320 coupled to the signal source 310, a microwave power splitter 330 coupled to the microwave amplifier unit 320, a controller 340 coupled to the microwave power splitter 330, and a plurality of radiating elements "$A_1$", "$A_2$", "$A_3$", "$A_4$" through "$A_N$" coupled to the controller 340. Microwave amplifier unit 320 may have any suitable input power and output power. Power splitter 330 may be implemented by a variety of components, including without limitation, coplanar striplines, coplanar waveguides, Wilkinson power dividers, and/or other suitable power dividers. In some embodiments, the power splitter 330 may be implemented by any suitable power divider that provides an equal or unequal power split at its output ports while substantially maintaining a predetermined phase relationship.

Controller 340 generally includes a plurality of phase shifters "$S_1$", "$S_2$", "$S_3$", "$S_4$" through "$S_N$". Controller 340 may include a number of processor units (not shown) coupled to the phase shifters "$S_1$", "$S_2$", "$S_3$", "$S_4$" through "$S_N$" for controlling output of one or more of the phase shifters "$S_1$" through "$S_N$" to provide a desired phase relationship of electrical signals in each channel of the phased antenna array 360. The processing units may include multiple processors and/or multicore CPUs and may include any type of processor capable of executing software, such as a microprocessor, digital signal processor, microcontroller, or the like.

Energy-delivery system 300 includes an electromagnetic window 390 disposed between the phased antenna array 360 and tissue "T". Electromagnetic window 390 may include a water bolus, or other dielectric material. In some embodiments, the electromagnetic window 390 is coupled in fluid communication with a coolant supply system 350 including a coolant source 355.

Coolant source 355 may be any suitable housing containing a reservoir of coolant fluid "F", and may maintain coolant fluid "F" at a predetermined temperature. For example, the coolant source 355 may include a cooling unit (not shown) capable of cooling the returning coolant fluid "F" from the electromagnetic window 390. Coolant fluid "F" may be any suitable fluid that can be used for cooling or buffering the electromagnetic window 390, e.g., deionized water, or other suitable cooling medium. Coolant fluid "F" may have dielectric properties and may provide dielectric impedance buffering for the phased antenna array 360. Various fluids may be used, e.g., liquids including, but not limited to, water, saline, perfluorocarbon, such as the commercially available Fluoriner® perfluorocarbon liquid offered by Minnesota Mining and Manufacturing Company (3M), liquid chlorodifluoromethane, etc. In other variations, gases (such as nitrous oxide, nitrogen, carbon dioxide, etc.) may also be utilized as the cooling fluid. In yet another variation, a combination of liquids and/or gases, including, for example, those mentioned above, may be utilized as the coolant fluid "F".

FIGS. 4 through 7 show the medical device 10 positioned for delivery of electromagnetic energy into tissue "T" shown with the pointing device 45 positioned in varied indicative orientations and shown with diagrammatic representations of radiation patterns of electromagnetic energy delivered into tissue by the medical device 10 responsive to the indicative orientations of the pointing device 45. It is to be understood that the indicative orientations of the pointing device 45 and the radiation patterns of electromagnetic energy are provided for illustrative purposes only, and that medical device 10 embodiments of the present disclosure may be utilized with many different indicative orientations of the pointing device 45 and many different radiation patterns.

FIG. 4 shows the tissue-contact surface 14 of the medical device 10 disposed adjacent to tissue "T" during a procedure, e.g., an ablation procedure, wherein the pointing device 45 is positioned in a first indicative orientation "$I_1$". For example, the first indicative orientation "$I_1$" may correlate with a 30° beam angle and an intensity level "1", e.g., low-intensity level. FIG. 4 shows a diagrammatic representation of a radiation pattern "$P_1$" of electromagnetic energy delivered into tissue "T" by the medical device 10 responsive to the first indicative orientation "$I_1$" of the pointing device 45 in accordance with an embodiment of the present disclosure.

FIG. 5 shows the tissue-contact surface 14 of the medical device 10 disposed adjacent to tissue "T" during a procedure wherein the pointing device 45 is positioned in a second indicative orientation "$I_2$". For example, the second indicative orientation "$I_2$" may correlate with a 0° beam angle and an intensity level "2", e.g., medium-intensity level. FIG. 5 shows a diagrammatic representation of a radiation pattern "$P_2$" of electromagnetic energy delivered into tissue "T" by the medical device responsive to the second indicative orientation "$I_2$" of the pointing device 45 in accordance with an embodiment of the present disclosure.

FIG. 6 shows the tissue-contact surface 14 of the medical device 10 disposed adjacent to tissue "T" during a procedure wherein the pointing device 45 is positioned in a third indicative orientation "$I_3$". For example, the third indicative orientation "$I_3$" may correlate with a 0° beam angle and an intensity level "3", e.g., high-intensity level. FIG. 6 shows a diagrammatic representation of a radiation pattern "$P_3$" of electromagnetic energy delivered into tissue "T" by the medical device responsive to the third indicative orientation "$I_3$" of the pointing device 45 in accordance with an embodiment of the present disclosure.

FIG. 7 shows the tissue-contact surface 14 of the medical device 10 disposed adjacent to tissue "T" during a procedure wherein the pointing device 45 is positioned in a fourth indicative orientation "$I_4$". For example, the fourth indicative orientation "$I_4$" may correlate with a −30° beam angle and an intensity level "1", e.g., low-intensity level. FIG. 7 shows a diagrammatic representation of a radiation pattern "$P_4$" of electromagnetic energy delivered into tissue "T" by the medical device 10 responsive to the fourth indicative orientation "$I_4$" of the pointing device 45 in accordance with an embodiment of the present disclosure.

Figure 8:
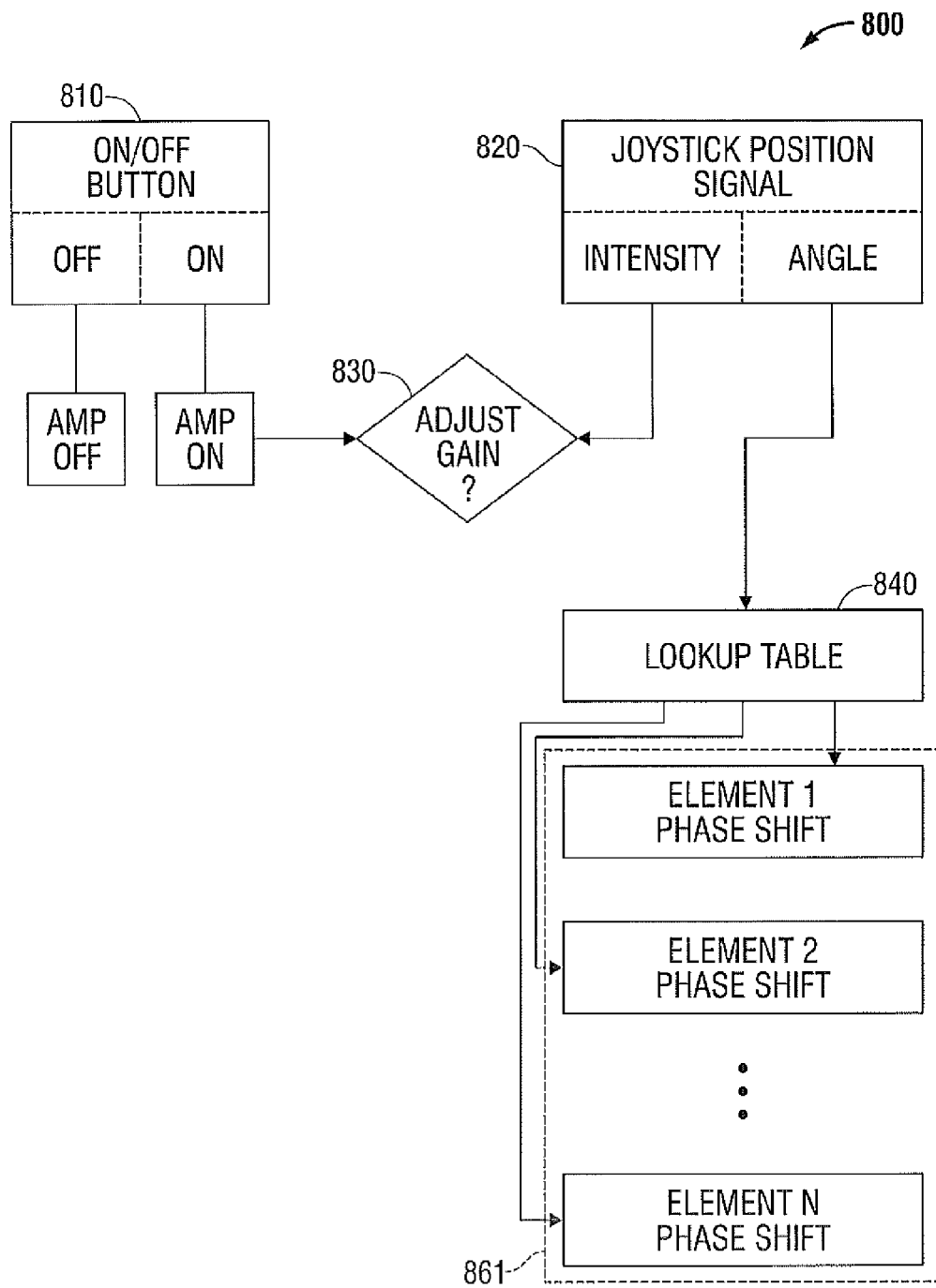
FIG. 8 is a schematic diagram of a control system in accordance with an embodiment of the present disclosure.

FIG. 8 is a schematic diagram of an embodiment of a control system 800 according to the present disclosure that is communicatively coupled with an on/off button 810 and configured to utilize a joystick position signal 820 indicative of intensity and angle of beam. As schematically-illustrated in FIG. 8, the control system 800 utilizes the joystick position signal 820 to determine whether to adjust antenna and/or amplifier gain 830 and/or to determine the phasing of the radiating elements (1 through N) of a phased antenna array 861, e.g., to allow the focal point of energy delivery in tissue to be varied in position in real-time and/or near real-time.

Control system 800 is configured such that when the on/off button 810 is in the "ON" state, adjustment of antenna and/or amplifier gain 830 is permitted, and when the on/off button 810 is in the "OFF" state, adjustment of antenna and/or amplifier gain 830 is not permitted. Joystick position signal 820 may be used in conjunction with a lookup table 840 to enable selective steering of the radiated beam of the phased antenna array 861. Lookup table 840 includes data representative of a mapping of the joystick positions to the phasing of the phased antenna array 861. As schematically-illustrated in FIG. 8, the control system 800 utilizes the lookup table 840 to determine the phasing of the radiating elements (1 through N) of the phased antenna array 861.

The above-described energy-delivery devices including an ultrasound transducer array and a phased antenna array are capable of directing energy into tissue, and may be suitable for use in a variety of procedures and operations. The presently-disclosed energy-delivery device including an ultrasound transducer array and a phased antenna array may be implemented using electromagnetic radiation at microwave frequencies, RF frequencies or at other frequencies.

The above-described energy-delivery device including an ultrasound transducer array and a phased antenna array according to embodiments of the present disclosure are adapted to be hand-holdable and include an ergonomically located user-interface.

The above-described electrosurgical systems provide clinicians the ability to visualize a tissue region during energy delivery into the tissue region. In the above-described electrosurgical systems, data acquired by the ultrasound transducer array may be outputted from the above-described energy-delivery device to an ultrasound imaging system, and may be outputted from the imaging system to one or more display devices and/or screens, which may be used by the clinician to visualize the targeted region in real-time and/or near real-time.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A medical probe device suitable for delivery of energy to tissue, comprising:
   a housing;
   a phased antenna array disposed within the housing, the phased antenna array emitting therapeutic electromagnetic energy;
   a user-interface disposed on the housing, the user-interface adapted to enable a user to selectively adjust the radiation pattern of electromagnetic energy delivered into a tissue region by the phased antenna array; and
   an ultrasound transducer array disposed within the housing, the ultrasound transducer array configured to acquire data representative of the tissue region during energy delivery into the tissue region by the phased antenna array.

2. The medical device of claim 1, wherein the housing includes:
   a body member defining an internal chamber configured to contain the ultrasound transducer device and the phased antenna array therein.

3. The medical device of claim 2, wherein the phased antenna array is operably coupled to an electrosurgical power generating source.

4. The medical device of claim 2, wherein the ultrasound transducer array is communicatively coupled with an ultrasound imaging system.

5. The medical device of claim 2, wherein the body member includes a distal end and defines a tissue-contact surface at the distal end.

6. The medical device of claim 5, wherein the tissue-contact surface includes a first region defining an ultrasound transmissive window.

7. The medical device of claim 6, wherein the ultrasound transducer array is operatively associated with the ultrasound transmissive window.

8. The medical device of claim 6, wherein the tissue-contact surface further includes a second region defining a microwave transmissive window.

9. The medical device of claim 8, wherein the phased antenna array is operatively associated with the microwave transmissive window.

10. The medical device of claim 1, wherein user-interface includes indicia thereon representative of at least one user-selectable parameter of electromagnetic energy delivery into tissue by the medical device.

11. The medical device of claim 10, wherein the indicia includes a first scale including indicia graduation marks and angle in degrees.

12. The medical device of claim 11, wherein the indicia further includes a second scale including indicia graduation marks and a series of consecutive positive integers indicative of energy intensity levels.

13. The medical device of claim 1, wherein the user-interface includes a pointing device.

14. The medical device of claim 13, wherein at least one parameter of electromagnetic energy delivery into tissue by the medical device is correlated to indicative orientations of the pointing device.

15. The medical device of claim 13, wherein the phased antenna array includes a plurality of radiating elements.

16. The medical device of claim 15, wherein at least one electrical signal outputted from the user-interface is responsive to a user-effected movement of the pointing device, and wherein the at least one electrical signal is used to determine phasing of the plurality of radiating elements.

17. A system, comprising:
   an electrosurgical power generating source; and
   a hand-holdable device operably associated with the electrosurgical power generating source, the hand-holdable device including:
      a phased antenna array emitting therapeutic electromagnetic energy;
      a user-interface disposed on the hand-holder device and adapted to enable a user to selectively adjust the radiation pattern of electromagnetic energy delivered into a tissue region by the phased antenna array; and
   an ultrasound transducer array configured to acquire data representative of the tissue region during energy delivery into the tissue region by the phased antenna array.

18. The system of claim 17, wherein the hand-holdable device further includes an electromagnetic window.

19. The system of claim 18, further comprising:
   a coolant supply system in fluid communication with the electromagnetic window.

* * * * *